(12) United States Patent
Lambert et al.

(10) Patent No.: US 9,005,769 B2
(45) Date of Patent: Apr. 14, 2015

(54) SUBSTRATE FOR WEAR-PROOF ORTHOPAEDIC JOINTS, OF NON FERROUS METAL WITH A NITRIDE-BASED COATING

(75) Inventors: Philippe Lambert, Chiasso (CH); Alessandro Farinotti, Rottofreno (IT)

(73) Assignee: Medacta International S.A., Castel San Pietro (CH)

( * ) Notice: Subject to any disclaimer, the term of this patent is extended or adjusted under 35 U.S.C. 154(b) by 111 days.

(21) Appl. No.: 13/695,605

(22) PCT Filed: May 11, 2011

(86) PCT No.: PCT/EP2011/002339
§ 371 (c)(1),
(2), (4) Date: Apr. 9, 2013

(87) PCT Pub. No.: WO2011/141169
PCT Pub. Date: Nov. 17, 2011

(65) Prior Publication Data
US 2013/0197649 A1    Aug. 1, 2013

(30) Foreign Application Priority Data

May 11, 2010   (CH) .......................................... 731/10

(51) Int. Cl.
| | |
|---|---|
| B32B 15/04 | (2006.01) |
| B21D 39/00 | (2006.01) |
| B32B 18/00 | (2006.01) |
| B32B 9/00 | (2006.01) |
| A61F 2/28 | (2006.01) |
| A61F 2/30 | (2006.01) |

(Continued)

(52) U.S. Cl.
CPC ............... *A61F 2/30* (2013.01); *A61F 2/30767* (2013.01); *A61F 2/32* (2013.01); *A61F 2002/30929* (2013.01); *A61F 2002/3098* (2013.01); *A61F 2310/00029* (2013.01); *A61F 2310/00886* (2013.01); *A61F 2310/00898* (2013.01); *A61L 27/045* (2013.01); *A61L 27/306* (2013.01); *A61L 2430/24* (2013.01); *C23C 28/04* (2013.01)

(58) Field of Classification Search
None
See application file for complete search history.

(56) References Cited

U.S. PATENT DOCUMENTS

| 4,284,687 A * | 8/1981 | Dreyer et al. ................. 428/336 |
| 5,593,234 A * | 1/1997 | Liston ........................... 384/492 |

(Continued)

FOREIGN PATENT DOCUMENTS

| DE | 100 11 583 A1 | 9/2000 |
| EP | 1923 079 A1 | 5/2008 |
| WO | WO 2011/141169 A1 | 11/2011 |

OTHER PUBLICATIONS

D.B. Lewis, "Chromium nitride/niobium nitride nano-scale multilayer coatings deposited at low temperature by the combined cathodic arc/unbalanced magnetron technique", dated 2005, 10 pages.

(Continued)

*Primary Examiner* — Humera Sheikh
*Assistant Examiner* — Seth Dumbris
(74) *Attorney, Agent, or Firm* — Hickman Palermo Becker Bingham LLP

(57) ABSTRACT

Substrates for joints for orthopaedic implants are described, wherein at least one of the sliding surfaces of non-ferrous metal alloys, in particular of cobalt, chromium, molybdenum alloys, has a coating consisting of niobium nitride nanolayers alternating with chromium nitride nanolayers, the lot being protected by a chromium nitride microlayer.

5 Claims, 3 Drawing Sheets

Figure 1:
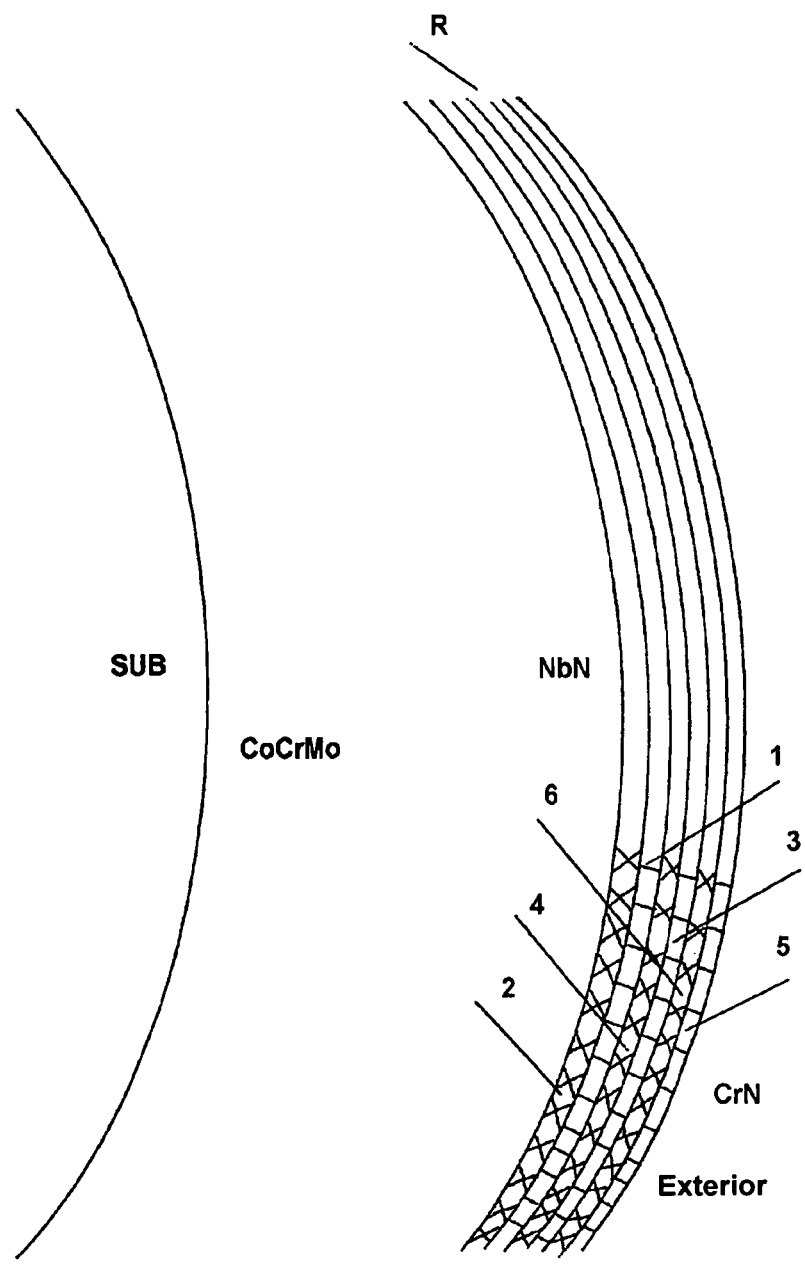

(51) Int. Cl.
    *A61L 27/04*     (2006.01)
    *A61L 27/30*     (2006.01)
    *C23C 28/04*     (2006.01)
    *A61F 2/32*     (2006.01)

(56) References Cited

U.S. PATENT DOCUMENTS

| | | | |
|---|---|---|---|
| 5,700,551 A | * | 12/1997 | Kukino et al. ............ 428/212 |
| 2005/0164041 A1 | | 7/2005 | Dunsmore |
| 2009/0074522 A1 | | 3/2009 | Graham |
| 2009/0290822 A1 | * | 11/2009 | Wilson et al. ............ 384/206 |

OTHER PUBLICATIONS

H.A. Jen, "Improvement of the corrosion resistance of PVD hard coating-substrate systems", dated 2000, 6 pages.

European Patent Office, "Office Action" in application No. PCT/EP2011/002339, dated Aug. 10, 2012, 10 pages.

European Patent Office, "International Search Report", in application No. PCT/EP2011/002339, dated Aug. 19, 2011, 4 pages.

* cited by examiner

SUBSTRATE FOR WEAR-PROOF ORTHOPAEDIC JOINTS, OF NON FERROUS METAL WITH A NITRIDE-BASED COATING

BACKGROUND OF THE INVENTION

The present invention relates to orthopaedic implants, in particular to hip and knee prostheses, substantially involving a metallic substrate with a nitride-based ceramic coating, which is biocompatible, hypo-allergenic, wear-proof and displays a low ion release and a high adhesion. More particularly, the invention relates to orthopaedic joint substrates of Co—Cr—Mo alloys coated with niobium nitride nanolayers, and chromium nitride nanolayers, protected by at least one chromium nitride microlayer.

STATE OF THE TECHNIQUE

For the most employed surgical procedures, for example THA (Total Hip Artroplasty), HR (Hip Resurfacing), TKA (Total Knee Arthroplasty) or UKA (Unicompartmental Knee Arthroplasty), the current, predominant concept of joint prosthesis is the so-called Metal on Polyethylene (MOP); in the case of the hip, a metallic femoral head moves against an acetabular shell. Among the disadvantages, the following can be cited: 1)—high wear of polyethylene, generating debris that triggers a biological response bringing to osteolysis [3]; 2)—a wear mechanism called "border lubrication" [8] whereby wear increases with the increasing diameter of the shell.

Alternatively, ceramic on ceramic (COC) joints are provided having low and more biocompatible wear debris, but the fragility of these aluminium and zirconium ceramics does not allow the big heads (36 mm and more) and the acetabular shells required in the (HR) procedure and desired in (THA).

Metal on metal (MOM) joints allow big components by virtue of the favorable lubrication regimen (called "full fluid film lubrication") [8], whereby wear is reduced with the increasing size of the head, but metal ions are released from the mass consisting of a cobalt-chromium alloy, as well as from wear debris, due to the corrosive effect of the long term contact with the body fluid. The amount of released ions increases with the size of the head, thus resulting in major concerns for the big heads used in hip resurfacing. These ions cause allergic reactions [8] called metal hypersensitivity or also metallosis, in about 2% of patients. Some recent clinical trials [18, 19, 20, 21, 22] attribute this reaction to osteolysis and to the short service time of the implant. However, the whole cause-effect mechanism has not been scientifically described [22] and therefore more exhaustive research is needed on metal allergy. Nowadays these conditions cannot be detected by presurgical selection tests. Again, another limiting factor of the MOM is potential long term genotoxicity of cobalt and chromium ions that can damage chromosomes depending on the dose, as it has been observed in in vitro studies [27]; here again more detailed research and specific clinical trials should confirm this risk. In spite of the lack of scientific evidence, both hypersensitivity and genotoxicity factors make the MOM philosophy less attractive despite its obvious tribological and duration advantages.

DESCRIPTION OF THE KNOWN ART

In order to remove doubts and inconveniences, resort is made to coating techniques, among which mention is made only of the following:

a) Nitride Coatings on steel and metal alloys have been carried out for several decades and given place to hard and wear-proof surfaces mainly in the cutlery and cutting tool industry in addition to that of components for diesel engines. This is due to the ease of deposition of current technologies such as (AEPVD, Arc Evaporative Vapour Deposition) also called (ACA, Cathodic Arc Deposition) [25].

b) Orthopaedic Joints Coated with Titanium Nitride (TiN).

Despite the biocompatibility of titanium, the employment of (TiN) coatings on medical devices and orthopaedic applications is quite limited.

The Swiss patent CH 621 476 (Hintermann) discloses titanium nitride (TiN) coatings on steel to increase the resistance to corrosion of sterilized cutting tools; the same Inventor, in U.S. Pat. No. 4,687,487, recommends the use of thin TiN coatings (2-3 micrometers) for orthopaedic implants on cobalt or titanium alloys in order to increase their resistance to sliding and wear.

Clinically successful application of a TiN coating has already been performed in the UKA (Unicompartmental Knee Arthro-Plasty) procedure on the distal femoral component since 1989; it has contributed to minimize the wear of PE in motion against the tibial plateau [1, 10]; however in said (THA) procedure the same coating applied on femoral heads against PE shells has not always been successful; currently, in fact, wear debris coming from the TiN layer damages hip joints as a third wear body [14, 15].

European patent EP 1 009 334 (K. Hamelijnck) [2] teaches that a very thin TiNbON layer (less than 1 micrometer) would give rise to a protective layer against wear for carbide prostheses containing CoCrMb, since the hardness of TiNbON is higher than that of carbides. The related ACCIS technology [26] has been applied on metallic femoral heads and on acetabular shells in said HR and THA procedures; these very thin coatings effectively reduce wear of incorporation, but are not resistant to wear particles of third hard bodies such as cement spikes of approx. 2 micron.

The major limit of TiN coating is given by its adhesion on CoCr alloys that results in cohesive ruptures [5] when it is deposited in coatings exceeding 5 micron. This can be explained by the stress resulting from thermal expansion differentials and from the absence of chemical affinity between the coating (Ti) and its substrate (CoCrMo). However, a 5-micron-thick coating will wear out in few years if it moves against a hard coating, specially in the presence of debris from a third body (cement particles etc.), the thickness of which could be of 2-3 micrometers. But this would limit the service time of the prosthesis to an unacceptable extent.

c) Orthopaedic Joints of Chromium Nitride (CrN).

EP 0 821 922 (C. Hubin) discloses a hip prosthesis with joints of CrN with thickness of 2 to 10 micrometers, which would be less fragile than the pre-ceramics and more resistant to wear than PE.

EP 1 404 257 teaches that CrN is better than TiN at resistance to cohesive rupture and hence it can be coated with coatings of 10 micrometers and more.

Even if CrN has not been used in orthopaedic industrial applications it has been the object of various in-vitro evaluations involving wear and hip joints simulators [3, 4, 5, 6, 7, 8, 9, 10, 11]. These in-vitro studies emphasize different aspects in comparison with alloys that are not coated with CoCr and TiN:

1) increased adhesion to the CoCr substrate in comparison with TiN [5];

2) a reduction in wearing rate of 22 to 36 times in comparison with a non-coated CoCr alloy, after 5 million cycles of normal run [4, 6]; and an even higher differential of load in the oscillation phase (higher load and microseparation) [7, 9]; the pivot-on-plateau wear simulator points out a higher wear differential (more than 100 times) between CrN and TiN (5).

3) cytotoxicity of wear debris 10 times lower (effect on L929 fibroblasts and U936 macrophages) than with non-coated CoCr [4].

Figure 2:
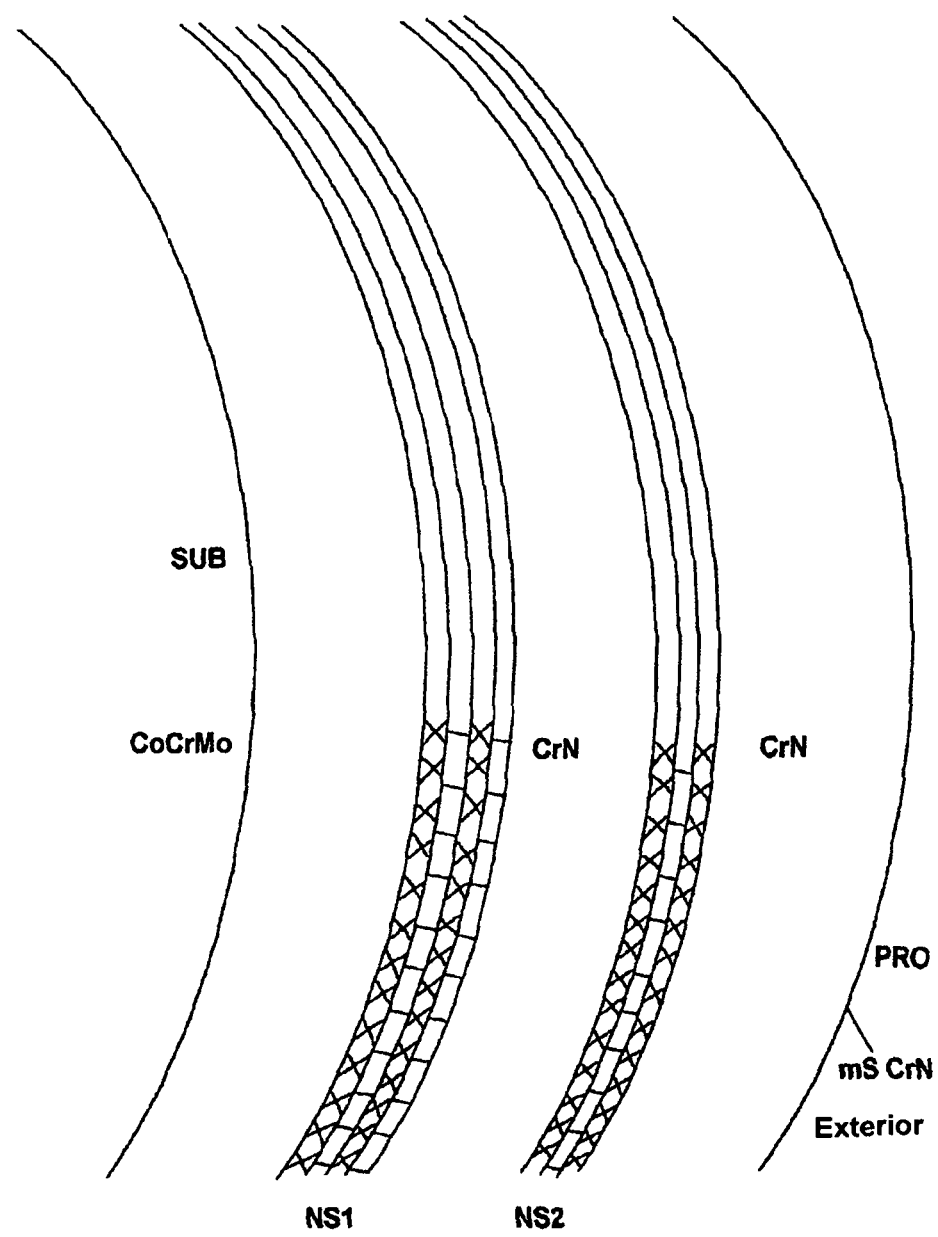

Despite all these advantages of non-coated metal and TiN coating, simulation studies on the hip joint emphasize a certain level of risk in the concentration of chromium ions in the simulated body fluid: if its level at normal rhythms, for example, is as suggested in FIG. 6 of [4], under high load and "microseparation", the same level is by far higher than the other ion concentrations, and close to the corresponding level on the non-coated metal-on-metal surfaces, as suggested in FIG. 2 of [7].

Additionally, a close examination of the joint surfaces after two million cycles of normal process on a hip simulator reveals isolated superficial small tears (6); while these can be eliminated by using the deposition process parameters, sensitivity towards fragility and lack of adhesion is noticed, which requires closer attention;

d) Chromium-Niobium Nitride (NbCrN); Known Art Related to the Composition.

Importance of the microstructure.

TiN and CrN obtained by means of the above described techniques (PVD) have a "columnar" structure characterized by voids and a relatively low superficial density. In this microstructure the big TiN or CrN crystals are not stabilized on their contours and this can result in voids and a relatively low superficial density as described in the U.S. Pat. No. 4,981,756; further, stress created by wear and/or corrosion can result in cracks in the crystal interface. On the other hand niobium nitride does not have a columnar structure and has therefore the ability to stabilize the crystal interface, resulting in an improvement at resistance to inter-crystalline corrosion, as described in the studies on steel alloys to prolong the lifetime of thermal treatment furnaces [28].

Additional empirical evidence of this effect of niobium or niobium nitride on the alloy microstructure can be retrieved in the U.S. Pat. No. 6,409,852 that discloses that an addition of 1% by weight Nb to a Ti-7.5 Mo alloy increases its hardness by 22%. Even more important are the modifications of nitride ceramics with NbN; Y. Yahisa found that the addition of NbN to TiN and to zirconium nitride results in harder and more durable discs for magnetic recording, mainly reducing the size of their grains [29].

In the EEC development project "Newcrome Brite/Euran", the consortium has created a super-lattice CrN/NbN to be deposited onto steel by physical vapour deposition (PVD) to replace the old and polluting electroplated chromium coating [30, 31, 32, 33]. In two distinct regions, compositions with high and low content of N, hardness values were nearly constant (3589 and 3600 Hk, respectively) [32] with respect to 2500 Hk of CrN [6]. These results from the consortium confirm Yahisa previous data [29] obtained on TiN and ZrN. They also prove that the microstructure may be influenced by the coating process parameters: at higher ion energies, the film structure changes from raw columnar to a more dense and smooth structure [32].

J. N. Tan [34], after further studying superlattices deposited by unbalanced magnetron sputtering, shows that Cr-rich compounds have lower friction and wear than the Nb-rich formulation.

e) Nitride/Chromium; Applications According to the Known Art

The U.S. Pat. No. 6,852,419 (G. Stachowiak) discloses a multi-layer coating for solar control consisting of an NbCrN layer able to reflect infrared, inserted between 2 dielectric layers. This intermediate layer was selected for its good corrosion resistance against warm alkaline solutions as well as for its good resistance to scraping.

In the U.S. Pat. No. 5,593,234 (M.-J. Liston) a support assembly is disclosed wherein at least one portion of its components is coated with hyper-hard superficial material of polycrystalline superlattice that can consist of NbN and CrN nanolayers. It is shown that the assembly is superior in duration than the non-coated metallic support (FIG. 6). In Patent No. DE 10 011 583 (L. Parenti) (corresponding to the Italian Patent Application PC 1999A 00009) a tool is described having a coating consisting of alternate CrN and NbN layers thus teaching that this combination allows to reduce grain sizes and therefore increase resistance to wear.

In the Publication PCT W09965537 (B. Starck) a superficial coating for stents is described, consisting of tantalum and niobium obtained by ion implant and selected among other coatings for its biocompatibility and ductility, higher than those of TiN.

In conclusion, the known art has experimented Ti and Cr nitrides in orthopaedic joints establishing the lack of adhesion to the substrate following the combined effect of wear and corrosion by the body fluid, due to the columnar microstructure. Not even thin monolayers of Ti Nb nitrides are efficient in protecting against wearing by hard third bodies. On the other hand, the deposition of NbN on non ferrous alloys such as CoCrMo has not been experimented in orthopaedic joints, although its biocompatibility and the well known absence of columnar structure in the case of deposition on steel.

At the best of our knowledge, the known art ignores a coating consisting of a combination of nanolayers of CrN and NbN.

SUMMARY OF THE INVENTION

The major objectives of the invention are now:
minimizing the amount of wear debris and metal ions formed in the joint articulation, thus reducing the risk of a hypersensitivity reaction that brings to inflammation and osteolysis;
preventing migrations of metal ions from the metallic mass deriving from corrosive effects caused by the long contact of body fluid with the naked metal thus reducing the risk of hypersensitivity;
providing more biocompatible wear debris: niobium ions, differently from cobalt, chromium and nickel do not induce negative biological response;
prolonging the lifetime of the implant, since in most cases the final failure of an orthopaedic implant occurs when the increased torque of the articulation exceeds the fixing resistance of the implant. The lower wearing rate of the coating keeps the torque low for a longer service time;
allowing the manufacturing of bigger low-friction joints.

The favorable film lubrication regimen provided by the hard, void-free coating reduces friction in the biggest joints requested on the market to increase the implant functions, and in particular the extent of movement.

The abovementioned objectives are reached with the substrates according to the claims, characterized by a coating containing niobium nitride nanolayers and chromium nitride nanolayers, protected by at least one chromium nitride microlayer.

DETAILED DESCRIPTION OF THE EMBODIMENTS OF THE INVENTION

Reference implants have characteristics like:

a) Substrate. The substrate material consists of the various Co, Cr, Mo alloys used in orthopaedics such as those complying with ISO 5832-405 832-6 05 832-12 regulations, that can be formed by casting or forging and contain a high level of carbon (0.35% and 0.014%, respectively), to undergo a heat treatment such as hot isostatic pressing (HIP) and solution annealing.

b) Implant. An exemplary hip implant with reconstructed surface includes a femoral and an acetabular component, the geometric characteristics of which are:

1) Diametral space: 150-250 micron (difference between diameters of an average shell and an average femoral head);

2) Deviation from sphericity: less than 10 micrometers;

3) Surface roughness index (Ra): less than 0.025 micrometers;

c) Prototypes. Prototype implants having contact surfaces to be coated satisfy the geometric specifications listed in point b).

d) Materials for Coating and Processing. Coating materials used in the examples, in particular for sliding surfaces (one on the head and one on the shell) are obtained by vapour deposition (AEPVD) in a Hauzer reactor, Flexicoat RTC 850 type with 3000 alternate 1-nanometer layers for the superlatex (SL) and one 3-micrometers layer for CrN.

As testing methods, the following were used:

1) Cavitation test, and scanning (exploring) electron microscopy:

2) Wear of the total hip prostheses as per ISO 14242-1 regulation Tribology—hip simulator;

3) Ionic Concentration of chromium and cobalt.

PREFERRED EMBODIMENTS

Descriptions of these test methods can be found in the literature cited in the references reported at the end of the examples.

It is understood that even if this invention is described with particular reference to the examples (and to FIGS. 1-3), the scope thereof cannot be intended as limited to what is exemplified and represented. Those skilled in the art will appreciate that the teachings thereof can be used in a wider variety of applications.

Example 1

Pins and Disc for Tribology Test (Pin-on-Disc) in Bovine Serum

Pins or needles of 6 mm of diameter and of 15 mm of length, with a half sphere end, of CoCrMo alloy according to ISO 5832-12 regulation (forged with low carbon content) and discs of 30 mm of diameter and 3 mm of thickness were machined and subjected to superficial polishing up to a roughness factor of 0.025 as per ISO 4287 regulation.

a) A portion of needles and discs was left without coating and called "control";

b) another portion of needles and discs was coated with 2.96 micrometers of Superlatex (SL) consisting of 2-nanometer-thick nanolayers of NbN and CrN obtained by vapour deposition (AEPVD), called "Superlatex". A final superficial polishing was carried out up to a roughness factor below 0.025 micrometers;

c) needles and discs were coated with 2.1 micrometers of Superlatex consisting of alternate 2-nanometer nanolayers of NbN and CrN, in contact with the substrate and an external 2.5-micrometer layer of CrN. All the layers were deposited by the AEPVD technique, called "Superlatex" SL/CrN. A final superficial polishing was carried out up to a roughness factor of 0.025 micrometers.

Samples were processed in a rotating tribometer immersed in a 25% bovine serum and 75% deionised water solution with 15 Newton load and with a Hertzian pressure of 1.572 GPa; the length of the track was 6,000 meters.

At the end of the test, the samples were analysed on a profilometer and the volume of wear was determined. The entity of wear expressed in $m^3/N \cdot m$ was calculated as well, see the following table:

|  | Wearing rate ($m^3/N \cdot m$) | Thickness of layer (micrometers) |
| --- | --- | --- |
| Non coated (control) | 480E−16: | None |
| Superlatex (SL) | 5.9E−16 | 2.96 |
| Superlatex/CrN (SL/CrN) | 6.8E−16 | 4.57 |

This shows the higher resistance to wear of Superlatex (SL)-based structures compared with non coated samples, however despite its slightly higher wear, SL/CrN was judged to be more promising due to the higher thickness of its coating. It is not currently possible to produce superlatex layers thicker than 3 micrometers without impairing their resistance. On the other hand, coatings with thickness lower than 3 micrometers are not able to ensure an implant lifetime longer than 20 years. Hence the use of superlatex without CrN is not viable for this application.

Example 2

Implant Prototype: Joints for Hip Resurfacing: Femoral Head and Acetabular Shell Coated with SL/CrN (Forged Substrate of CoCrMo Alloy with Low Carbon Content)

The example discloses a device for hip resurfacing consisting of:

1)—a femoral head, the substrate of which is made of CoCrMo alloy according to ISO 5832-12; and 2)—an acetabular shell made of the same metallic substrate.

Femoral heads and shells were either left intact and used as reference or coated with SL/CrN having a total thickness of 5.3 micrometers, of which 2.6 micrometers of SL consist of alternate nanolayers (each one 2-nanometer thick) of niobium and chromium nitride, and 2.7 micrometers of CrN; all the layers were deposited by AEPVD technique. A final polishing was also carried out to reduce superficial roughness below 0.025 micrometers.

Prototypes were then subjected to an acoustic test of "sonication" to evaluate inter-layer adhesion (see Sonication Texts) and to a simulation of the hip wear to measure wear itself and ionic release in the presence of a simulated body fluid.

Samples:

Non coated control: B and G pairs

Coated with SL/CrN: L and M pairs

Femoral head coated with Superlatex/CrN: V02523

Femoral head coated with pure CrN (4 micrometers AEPVD): V02580

Results of the Tests:

Test methods (see the attached References with detailed description of the methods):

a) Cavitation and scanning electron microscopy (here called "adhesion") test;

b) Wear of the total hip prosthesis according to ISO 14242-1, Tribology: hip simulator here called "wear" after one million cycles;

c) Ionic concentration of chromium and cobalt here called "metal ions" after one million cycles.

|  | Non coated pairs | | Coated pairs | | Coated head SL/CrN | Coated head CrN |
| --- | --- | --- | --- | --- | --- | --- |
| Test | B | G | L | M | V02523 | V02580 |
| Wear (mgr) | 2.8 | 2.8 | 1.5 | 2.6 | | |
| Metal ions (microg/l) | | | | | | |
| Co | 1185 | 2346 | 7.92 | 21.6 | | |
| Cr | 437 | 813 | 53.2 | 73.4 | | |
| Adhesion Weight loss (mgr) | | | | | 0.57 | 1.8 |
| SEM | | | | | No delamination | Delamination |

Conclusion:

Surprisingly, SL/CrN double coating is superior to the non-coated implants in the release of cobalt ions by 2 orders of magnitude, in the release of chromium ions by 1 order of magnitude and exhibits 30% lower gravimetric wear. It also shows a low tendency to delaminate from the substrate after a test of 2 hours exposure to ultrasonic energy in comparison to direct CrN coating obtained by AEPVD technique.

It is also surprising that coating according to this invention provides a much larger reduction of the Co and Cr ion release of the reduced wear debris; this suggests that wear debris is less susceptible to ionization in the body fluid.

Example 3

Implant Prototype: Hip Joints Resurfacing: Femoral Head and Acetabular Shell Coated with Superlatex/CrN (CoCrMo Substrate Obtained by Casting with High Carbon)

This time the same double coating is deposited on an ISO 5832-4 CoCrMo alloy, parameter and test method being equal to those cited in example 2.

Samples: Coated sample SL/CrN: N pair

Head (head from high carbon melt-casting) 60347/14

Results of the Tests: reference coating with low carbon forged substrate as per example 2) in comparison with high carbon cast substrate.

|  | Coating on LCF (example 2) | | | Coating on HCC (example 3) | |
| --- | --- | --- | --- | --- | --- |
| Test | L | M | V2523 Head | N | 60347/14 Head |
| Wear (mgr) | 1.5 | 2.6 | | 2.6 | |
| Metal ions (microg/l Co) | 7.92 | 21.60 | | 33.6 | |
| Cr | 53.20 | 73.40 | | 11.00 | |
| Adhesion weight loss (mgr) | | | 0.57 | | 0.73 |
| SEM | | | No delamin. | | No delamin. |

Conclusions:

There is no big difference between SL/CrN coating on a substrate obtained by high carbon casting (HCC) and on a low carbon forged substrate (LCF), both coatings are superior to the non coated materials; however, with all the measured parameters (wear, ion release and adhesion), LCF substrate gives slightly better results.

DESCRIPTION OF THE INVENTION AND ILLUSTRATIVE DRAWINGS

Figure 3:
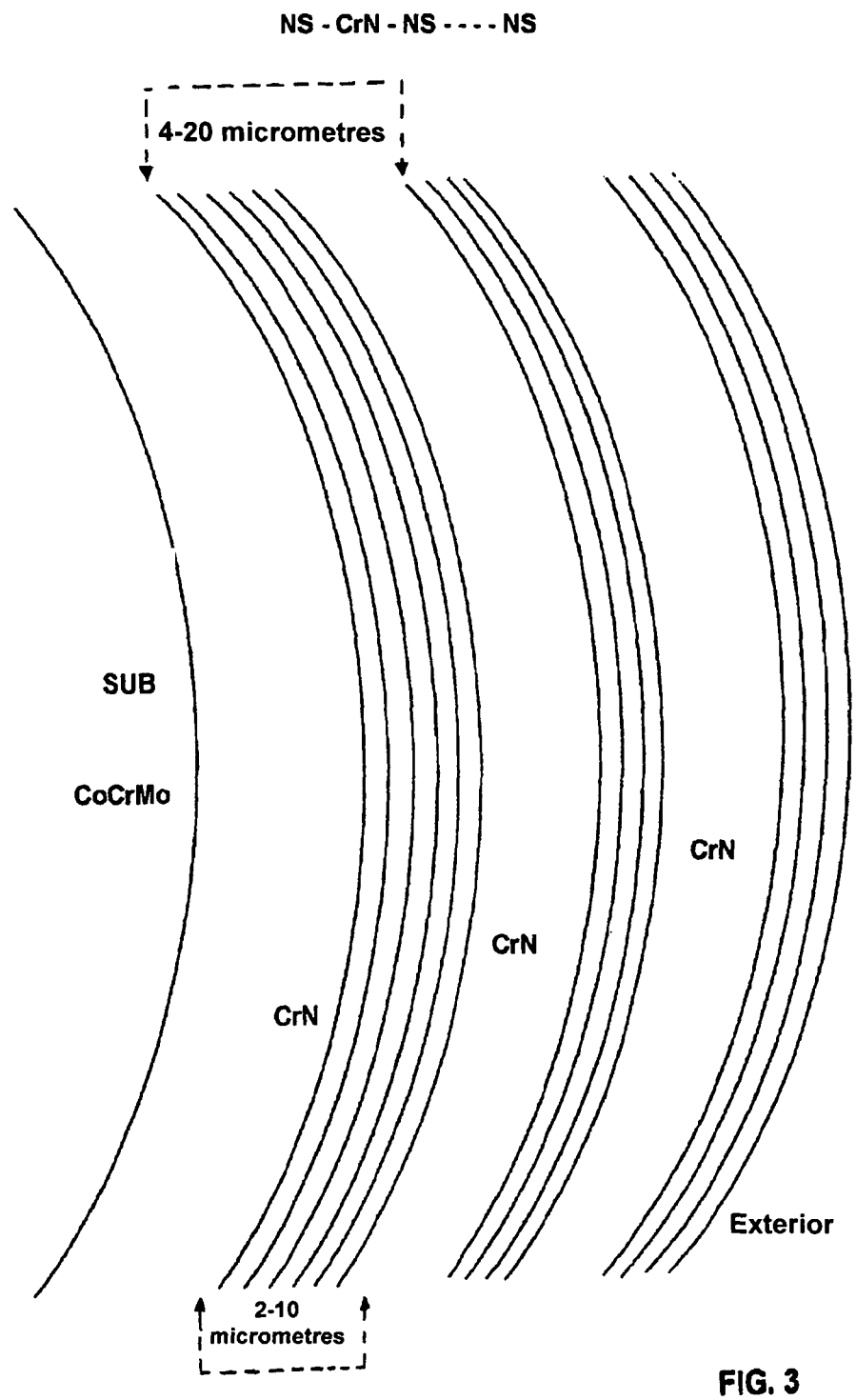

A simpler and more synthetic approach to the spirit and development of the present invention is represented in schematic FIGS. 1-3.

In FIG. 1 (reference example) an orthopaedic substrate SUB is represented, on which a coating R was applied consisting of several niobium nitride nanolayers (NbN), 2, 4, 6 etc. etc. alternating with several chromium nitride layers (CrN) 3, 5, 7 etc. etc., which was satisfactorily experimented on non-orthopaedic bodies. Found values were satisfactory as to delamination, but unsatisfactory as to wear. The layer must actually have a global thickness of a maximum 3 micrometers that is not sufficient to prevent an overall penetration of wear during the lifetime of the implant (see example 1). This demonstrates that a coating that is safely used in a non-orthopaedic field is not suitable to be extended as is to the orthopaedic field. Overcoming the prejudice of this counter-teaching, the Applicant continued his research and unexpectedly found that already with a global structure or sequence as per FIG. 2, consisting of NbN nanolayers alternating with CrN nanolayers and preferably of a protective mSCrN microlayer (PRO) spaced from the last (more external) chromium nitride nanolayer, a first critical improvement at wear and ion release is obtained. Said structure or sequence, for example as in FIG. 2, can be advantageously repeated one to twenty times. In FIG. 2 two alternate SL nanolayers NS1, NS2, are represented but their number can be by far higher than two. The distance of the last CrN layer from the protective microlayer is preferably comprised between 2 and 10 micrometers.

In FIG. 3 substrate SUB, 3 groups of alternating NS nanolayers separated by a protective 2 to 4 micron thick mSCrN microlayer are represented in an exploded form. As indicated in FIG. 3 the first and second layer can have 2 to 10 nanometers thick nanolayers; the distance between the first two nanolayers will range between 4 and 20 micrometers.

REFERENCES

[1] G. Saxler and al., Medium-term results of the AMC-unicompartmental knee arthroplasty, The Knee 11 (2004) 349-355.

[2* ACCIS U.S. Pat. No. 6,120,545 and van Straten Medicai Product portofolio.

[3] J. Fisher and al., An in vitro study of the reduction in wear of metal-on-metal hip prostheses using surface-engineered femoral heads, J. Engineering in Medicine Vol 216 Part H.

[4] J. Fisher and al., New Bearing Surfaces: What does the future hold? Seminar in arthroplasty, vol 14, no 2 (april) 2003: pp 131-139.

[5] S. Williams and al., in Vitro analysis of the wear, wear debris and biological activity of surface-engineered coatings for use in metal-on-metal total hip replacements, J. Engineering in Medicine Vol. 217 Part H.

[6] J. Fisher and al., Wear of surface engineered metal-on-metal hip prostheses, J. of Materials Science: materials in Medicine 15 (2004) 225-235.

[7] S. Williams and al., The Influence of Swing Phase loading on wear of Metal-on-Metal and CRN surface modified total hip replacements, ISTA 2003 volume 1 pp 143-149.

[8] J. L. Tipper and al., The science of metal-on-metal articulation, Current Orthopaedics (2005) 19, 280-287.

[9] S. Williams and al., Comparative wear under different conditions of surface-engineered Metal-on-Metal bearings for total hip arthroplasty, J. of Arthroplasty Vol. 19 No 8 Suppl. 3 2004.

[10] A. Kamali and al., Wear of ultrahigh-molecular-weight polyethylene against titaniumnitride-coated counterfaces, J. Engineering Tribology Vol. 219 Part J.

[11] G. H. Isaac and al., Metal-on-Metal bearings surfaces: materials, design, optimization and alternatives, J. Engineering in Medecine Vol. 220 (26 May 2005).

[12] J. Fisher, Tribology of new alternative bearings, AAOS, march 22-26, 2006 Chicago.

[13] Finsbury Adept Hip system Technical bulletin www.finsbury.org.

[14] M. K. Harman and al., Wear analysis of a retrieved hip implant with Titanium nitridecoating, J. of Arthroplasty vol. 12 N08 1997.

[15] M. T. Raimondi and al., The in-vivo wear performance of prosthetic femoral heads with Titanium nitridecoating; Biomaterials 21 (2000) 907-913.

[16] C. Hubin and al., Hip prosthesis joint component with particulate trap, FR 2 751 526 French Patent deemed to be withdrawn.

[17] P. Hatto and al., an orthopaedic joint prosthesis, EP 1 404 257, european patent application.

[18] H. G. Willert and al., Metal-on-Metal Bearings and Hypersensitivity in patients with Artificial Hip Joints, JBJS (American) 2005; 87: 28-36.

[19] Y. S. Park and al., Early Osteolysis Following Second-Generation Metal-on-Metal Hip replacement, JBJS (American) 2005; 87: 1515-1521.

[20] I. Milosev and al., Survivorship and retrieval analysis of Sikomet Metal-on-Metal Total Hip Replacements, JBJS (American) 2006; 88: 1173-1182.

[21] P. Korovessis and al., Metallosis after contemporary Metal-on-Metal Total Hip Arthroplasty, JBJS (American) 2006; 88): 1183-1191.

[22] J. J. Jacobs and al., Loosening and osteolysis associated with Metal-on-Metal Bearings: A local effect of metal hypersensitivity? JBJS (American) 2006; 88: 1171-1172.

[23] P. Hatto and al., An Orthopaedic Joint Prosthesis; European Patent EP 1 404 257.

[24] C. Hubin and al., Hip prosthesis joint component with particulate trap, European Patent EP 0 821 922.

[25] Hauzer's thin film deposition technologies, www.hauzer.nl

[26] Van Straten Product Portofolio, www.vanstraten.net

[27] B. Daley and al., Wear debris from hip and knee replacements causes chromosomal damage in human cells in Tissue cultures; JBJS (UK) 2004, 86B: 598-606.

[28] S. Y. Shipitsyn and al., Improvement in the life of cast equipment for heat-treatment furnaces, J. of Metal Science and Heat treatment, vol. 23, nr 12, December 1981.

[29] Y. Yahisa and al., microstructure and mechanichal properties of metal-alloy nitride (M1 M2)N overcoats for rigid disks, IEEE transactions on magnetics, vol. 26, no 5, September 1990.

[30] Newchrome Brite/Euram EEC project BRPR960 329; coordinator Hauzer Coating centrum www.cordis.europa.eu

[31] P. ed. Hovsepian and al., chromium nitride/niobium nitride superlattice coatings deposited by combined cathodic-arc/unbalanced magnetron technique; Surface and Coatings Technology 116-119 (1999) 727-734.

[32] D. C. Cameron and al., structural variations in CrN/NbN superlattices, Surfaces and Coatings Technology, volumes 142-144, July 2001, Pages 567-572.

[33] M. L. Tomlinson, The influence of coating composition on the corrosion performance of stainless steel, UMIST Manchester seminars, Oct. 28, 1998.

[34] J. N. Tan and al., Deposition and characterization of (Nb, Cr) N thin films by unbalanced magnetron sputtering, Surfaces and Coatings Technology, Volumes 167, Issues 2-3, 22 Apr. 2003, Pages 154-160.

[35] P. E. Hovsepian and al., Recent progress in large scale manufacturing of multiplayer/superlattice hard coatings; Surfaces and coatings Technology 133-134 (2000)166-175.

[36] R. Torrecillas, INCAR-CSIS, <<Extending the life span of orthopaedic implants: development of ceramic hip and knee prostheses with improved zirconia toughened alumina nanocomposites>> BIOKER PF5EEC project.

The invention claimed is:

1. A substrate for joints for orthopaedic implants, wherein at least one of one or more sliding surfaces of a CoCrMo alloy, comprises a plurality of coatings of nitride layers, characterized in that each of said coatings contains niobium nitride nanolayers alternated with chromium nitride nanolayers, protected by a chromium nitride microlayer.

2. The substrate according to claim 1, wherein the niobium nitride nanolayers alternated with the chromium nitride nanolayers are repeated 1 to 10 times.

3. The substrate according to claim 1, wherein the niobium nitride nano-layers alternated with the chromium nitride nanolayers are repeated 11 to 20 times.

4. The substrate according to claim 1, characterized in that a distance between a last, most external one of the chromium nitride nanolayers and a chromium nitride microlayer is between 2 and 10 micrometers, a thickness of each of the nanolayers is between 1 and 10 nanometers, and a sum of thicknesses of the nanolayers is between 2 and 10 micrometers.

5. The substrate according to claim 2, characterized in that a distance between a last, most external one of the chromium nitride nanolayers and a chromium nitride microlayer is between 2 and 10 micrometers, a thickness of each of the nanolayers is between 1 and 10 nanometers, and a sum of thicknesses of the nanolayers is between 2 and 10 micrometers.

\* \* \* \* \*